US011497510B2

(12) United States Patent
Ingman et al.

(10) Patent No.: US 11,497,510 B2
(45) Date of Patent: Nov. 15, 2022

(54) ELECTROMAGNETIC INTRAMEDULLARY NAIL SCREW POSITIONING SYSTEM

(71) Applicant: AUSTOFIX GROUP LIMITED, South Australia (AU)

(72) Inventors: Anthony Mark Ingman, South Australia (AU); Chris Henry, South Australia (AU)

(73) Assignee: AUSTOFIX GROUP LIMITED, South Australia (AU)

( * ) Notice: Subject to any disclaimer, the term of this patent is extended or adjusted under 35 U.S.C. 154(b) by 263 days.

(21) Appl. No.: 16/639,048

(22) PCT Filed: Aug. 14, 2018

(86) PCT No.: PCT/AU2018/000134
§ 371 (c)(1),
(2) Date: Feb. 13, 2020

(87) PCT Pub. No.: WO2019/033141
PCT Pub. Date: Feb. 21, 2019

(65) Prior Publication Data
US 2020/0222065 A1    Jul. 16, 2020

(30) Foreign Application Priority Data
Aug. 15, 2017  (AU) .............................. 2017903273

(51) Int. Cl.
*A61B 17/17*  (2006.01)
*A61B 34/20*  (2016.01)
(Continued)

(52) U.S. Cl.
CPC ...... *A61B 17/1707* (2013.01); *A61B 17/1725* (2013.01); *A61B 34/20* (2016.02);
(Continued)

(58) Field of Classification Search
CPC . A61B 17/17; A61B 17/1707; A61B 17/1725; A61B 34/20; A61B 90/96; A61B 90/94
See application file for complete search history.

(56) References Cited

U.S. PATENT DOCUMENTS 5,584,838 A     12/1996  Rona et al.
2005/0070916 A1  3/2005  Hollstien et al.
(Continued)

FOREIGN PATENT DOCUMENTS

CN  2671510   1/2005
EP  0589592   3/1994
(Continued)

OTHER PUBLICATIONS

International Search Report and Written Opinion for International (PCT) Patent Application No. PCT/AU2018/000134, dated Oct. 3, 2018, 16 pages.

Primary Examiner — Christopher J Beccia
(74) Attorney, Agent, or Firm — Sheridan Ross P.C.

(57) ABSTRACT

An electromagnetic intramedullary nail screw positioning system is used to assist an orthopaedic surgeon to correctly aligned a screw drill guide with a screw receiving aperture in an intramedullary nail during surgery. However due to the large number of different types of intramedullary nail, the system must be calibrated during each surgery. An improved calibration system is described that no longer requires the surgeon to perform the calibration during the surgery in order to save time and improve robustness. The system is periodically calibrated and a memory stores offset information for a range of nails types relative to a reference nail. During surgery, the surgeon enters a nail identifier, and the system looks up the associated offset and applies this offset to the measured signals to guide alignment of the screw drill guide with the screw receiving aperture.

19 Claims, 7 Drawing Sheets

(51) Int. Cl.
  *A61B 90/94*   (2016.01)
  *A61B 90/96*   (2016.01)
  A61B 17/72    (2006.01)
  A61B 17/00    (2006.01)
  A61B 17/56    (2006.01)

(52) U.S. Cl.
  CPC .............. *A61B 90/94* (2016.02); *A61B 90/96* (2016.02); *A61B 17/7241* (2013.01); *A61B 2017/00115* (2013.01); *A61B 2017/00725* (2013.01); *A61B 2017/564* (2013.01); *A61B 2034/2048* (2016.02); *A61B 2034/2051* (2016.02); *A61B 2034/2072* (2016.02)

(56) References Cited

U.S. PATENT DOCUMENTS

| | | |
|---|---|---|
| 2005/0080427 A1 | 4/2005 | Govari et al. |
| 2005/0261700 A1 | 11/2005 | Tuma et al. |
| 2009/0088756 A1 | 4/2009 | Anderson |
| 2010/0152573 A1 | 6/2010 | Ritchey et al. |

FOREIGN PATENT DOCUMENTS

| | | |
|---|---|---|
| WO | WO 2010/129141 | 11/2010 |
| WO | WO 2012/051512 | 4/2012 |
| WO | WO 2012/109760 | 8/2012 |

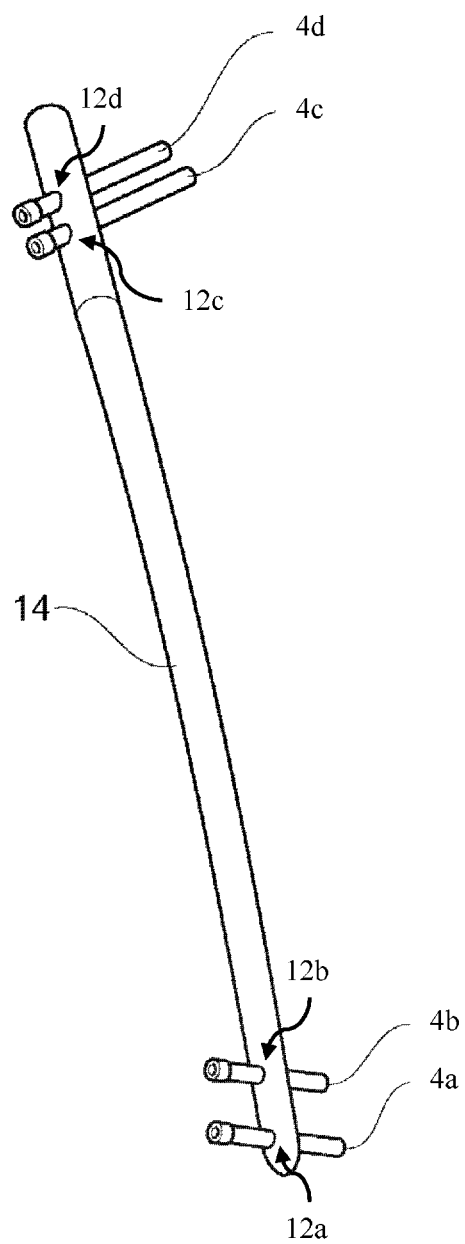
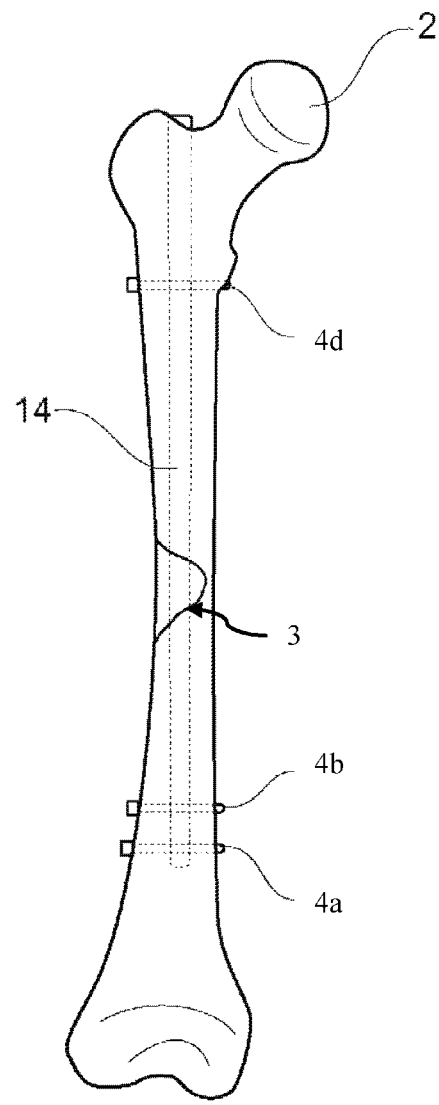
Figure 1A
Figure 1B

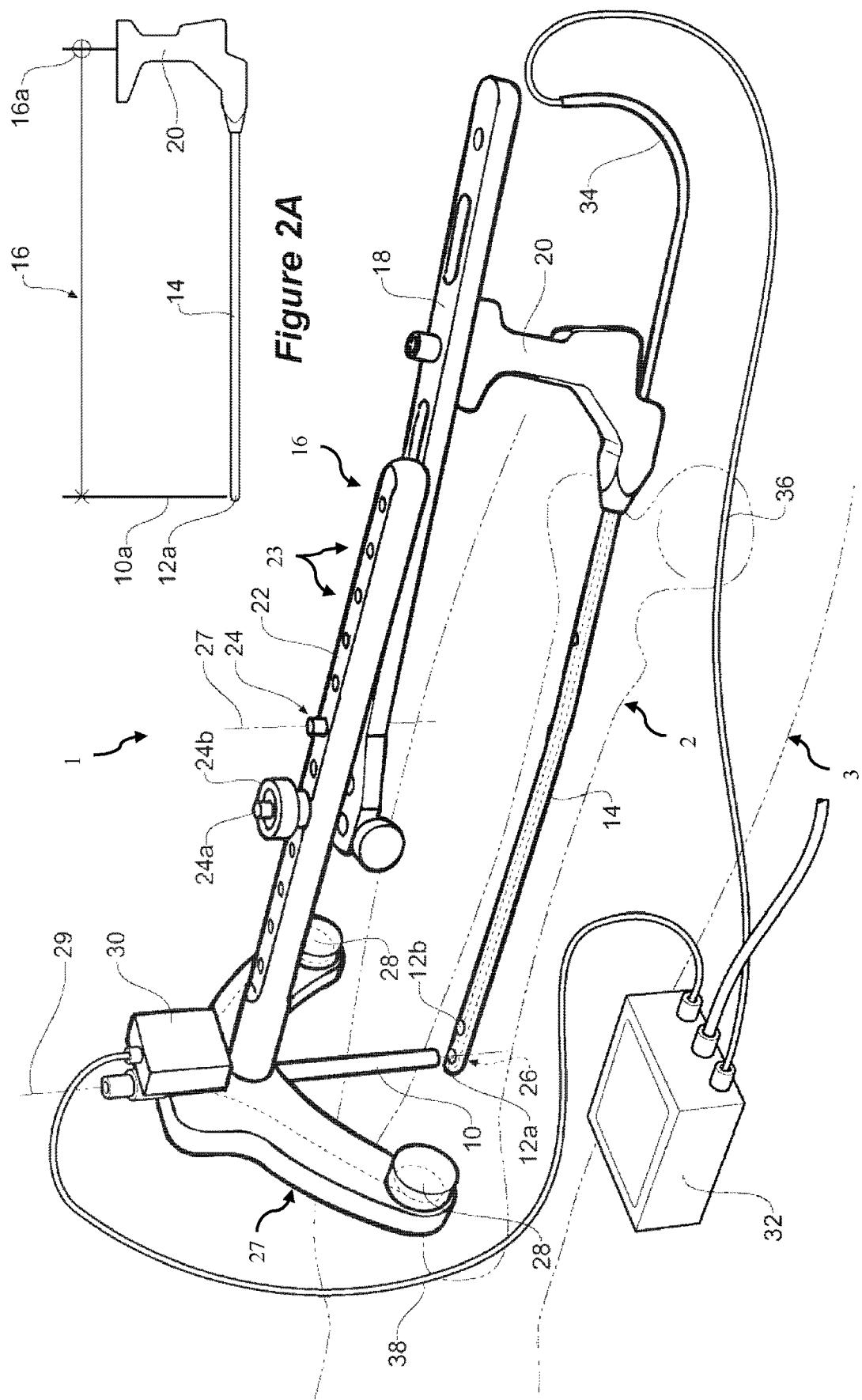

ELECTROMAGNETIC INTRAMEDULLARY NAIL SCREW POSITIONING SYSTEM

CROSS-REFERENCE TO RELATED APPLICATIONS

This application is a national stage application under 35 U.S.C. 371 and claims the benefit of PCT Application No. PCT/AU2018/000134 having an international filing date of 14 Aug. 2018, which designated the United States, which PCT application claimed the benefit of Australian Provisional Patent Application No. 2017903273 titled "ELECTROMAGNETIC INTRAMEDULLARY NAIL SCREW POSITIONING SYSTEM" and filed on 15 Aug. 2017, the contents of each of which are hereby incorporated by reference in their entireties.

TECHNICAL FIELD

The present disclosure relates to orthopaedic surgery. In a particular form the present disclosure relates to using electromagnetic devices for location detection of a portion of an orthopaedic device.

BACKGROUND

A common orthopaedic surgical technique for treating diaphyseal fractures of long bones is to insert an IntraMedullary Nail (IMN) into the intramedullary space of the bone. The bone is then fixed to the nail using screws which engage with and/or pass through apertures in the nail. Apertures are typically located at least at the proximal and distal ends of the nail (in this context proximal refers to the point of entry of the nail into the bone). A difficulty associated with this procedure is that once the nail is inserted into the bone, the exact location of these apertures will be hidden by the surrounding tissue and bone, making identification of the drilling locations difficult.

Standard surgical procedure is thus to use X-ray imaging is obtain a series of still images, or real-time fluoroscopic imaging, to identify the relative locations of the bone, nail and apertures to allow the correct placement and alignment of orthopaedic devices during surgery. However a significant downside of this radiological approach is that this practice typically exposes the surgeon and surgical staff to potentially hazardous radiation exposure (particularly to the hands). Furthermore, the radiation and detection equipment is inconvenient to assemble or has to be brought into the operating theatre. Although the images obtained are helpful, they can take a long period of time to generate to be useful because they are still imprecise. This adds to the surgical time as well as to the expense of the surgical procedure.

Various approaches have been used to address these issues. One approach is to use a jig attached to the IMN which is designed to guide a drill to ensure correct interlocking screw placement through bone to the IMN located within the bone without the need for X-ray imaging to confirm placement of the screw. Whilst drill alignment jigs are known to successfully target the proximally located screw hole/s, the distal end of the IMN often undergoes significant deflection as it is inserted into the bone. This introduces significant distal jig alignment errors and so requires one or more X-rays to be taken to identify the exact location of the distal aperture and to ensure or confirm that the drill guide is positioned correctly before the distally located holes in the bone are made.

Another variation utilises an additional incision and hole drilled orthogonally to the nail. An anterior aiming hook is inserted through this hole to physically locate the IMN and correct alignment of the guide for IMN deflection. Whilst this approach may reduce or eliminate the need for X-ray images, it has the disadvantage of requiring a more complex alignment jig and creates additional trauma for the patient.

Various electromagnetic based locating techniques have also been explored. For example one electromagnetic based approach that has been suggested is static magnetic field targeting which involves detecting of the location of a permanent magnet inserted in the IMN. Active electromagnetic systems use electromagnetic transmitters and receivers, at least one of which is located or inserted within the nail to assist in identifying.

One difficulty with electromagnetic based approaches is that they must be sufficiently sensitive to detect the location of a small void in a metallic component. As such they are sensitive both to distortion of the electromagnetic field due to the surgical devices itself, either due to the device being ferromagnetic (ie steel nails) or due to the generation of eddy currents in conductive non-ferromagnetic materials (eg titanium nails), as well as the presence of nearby conductors or electromagnetic fields. The exact nature of the distortion will change from surgery to surgery depending upon the length of the nail and material, as well as the relative location of surgical equipment. For example practical investigations into the static magnetic field targeting approach found the system had insufficient targeting accuracy, with large offsets due to similarly sized magnetic fields from other sources and the nearby ferromagnetic materials, which adversely influenced the targeting preventing reliable use of this approach.

Active systems have performed better. For example in one system the IMN includes a central shaft (ie is cannulated) and a sensor is inserted a known distance into the shaft. Two transmitters are located on a support arm which is secured to an alignment jig around a drill sleeve. A microcontroller processes the signals and a display module displays a representation of the location of the nail and apertures along with the current drilling location. The drilling jig can then be adjusted until the current drilling location aligns with the target aperture. Whilst this system has proved effective, one disadvantage is that calibration of the system must be performed during surgery. This involves the surgeon (or other surgical staff) inserting the sterile nail into the jig, inserting the sensor into the shaft of the nail, fixing the support arm to the jig, and then adjusting the jig until the drilling sleeve in the support arm is aligned with the target aperture in the nail. At this point the user presses a set button to inform the controller system is aligned. The system is then disassembled, and the nail is inserted into the bone of the patient followed by insertion of the sensor. The jig is then reassembled on the patient with the support arm, and the calibrated system is used to align the drilling sleeve with the target aperture using the display module. Once the drilling sleeve is aligned, the surgeon drills the holes and inserts the screws.

This calibration process is less than ideal, as it must be performed during surgery, thus taking up valuable time. Further it requires insertion of the sterilised nail into the sterilised jig before being placed in the patient, increasing the risk of possible contamination of the nail. Further it places the onus on the surgeon or surgical staff to correctly perform the calibration process. In particular it requires the procedure to be performed away from metallic components and electromagnetic sources which may distort the electromagnetic field around the nail and thus lead to an erroneous calibration. For example ideally the calibration is performed in free space (eg in the air) away from surgical equipment, which may not necessarily occur if performed by a surgeon or surgical staff during the surgical procedure.

There is thus a need to provide an improved electromagnetic targeting system and calibration method, or at least to provide a useful alternative to existing systems and methods.

SUMMARY

According to a first aspect, there is provided a control apparatus for an electromagnetic intramedullary nail screw positioning system for positioning a drill guide arrangement usable to guide a drill towards a screw receiving aperture in an intramedullary nail, the apparatus comprising:

at least one processor, at least one memory, and a user interface, wherein the memory comprises a plurality of offset values, each offset value associated with a intramedullary nail identifier, and the memory comprises instructions to cause the processor to:

receive an intramedullary nail identifier from a user via the user interface;

send at least one control signal to one or more signal transmission and receiving circuits to transmit one or more signals from at least one transducer;

receive at least one receive signal from one or more signal transmission and receiving circuits from at least one transducer;

estimate the position of the transducer positioned adjacent the screw receiving aperture relative to the longitudinal axis of the drill guide arrangement using the at least one receive signal;

determine an offset value using the received an intramedullary nail identifier;

apply the determined offset to the estimate the position of the transducer to obtain an updated estimate; and indicate the updated estimate of the position of the transducer positioned adjacent the screw receiving aperture relative to the longitudinal axis of the drill guide arrangement using the user interface.

In one form, the received nail identifier comprises one or more of a nail diameter, nail composition, nail length and nail side. In another form the received nail identifier comprises a product code or catalogue number. In another form the control apparatus comprises a barcode scanner, and the nail identifier is received from the barcode scanner.

In one form the plurality of offset values are stored as an offset table in the at least one memory, wherein each offset is associated with a nail identifier. In a further form, the offset values are obtained from a reference calibration process performed prior to a surgical procedure, wherein the reference calibration process comprises:

performing a reference calibration using a reference nail with an electromagnetic intramedullary nail screw positioning system;

for each nail in a set of nails types, where each type comprises a unique combination of nail diameter, nail composition and nail length, measuring an alignment offset of an inserted nail in the electromagnetic intramedullary nail screw positioning system with respect to the reference nail; and storing the set of measured alignment offsets in the at least one memory with each associated nail type.

In one form the control apparatus comprises a display, and indicating the updated estimate of the position of the transducer comprises visually indicating the updated estimate of the position of the transducer positioned adjacent the screw receiving aperture relative to the longitudinal axis of the drill guide arrangement.

According to a second aspect, there is provided an electromagnetic intramedullary nail screw positioning system comprising:

a) a framework including:
an intramedullary nail holder adapted to attach to an intramedullary nail;
an elongate extension member extending from the intramedullary nail holder adapted to allow movement of the elongate extension member relative to the intramedullary nail holder; and
an elongate drill guide arrangement associated with the extension member so that the longitudinal axis of the drill guide arrangement is orientated substantially towards the intramedullary nail;

b) at least two transducers, one transducer positioned in the intramedullary nail adjacent one of the screw apertures, and at least one transducer positioned relative to the elongate extension member;

c) one or more signal transmission and receiving circuits for communicating one or more signals with a respective transducer for respectively transmitting and receiving the one or more signals;

d) a control apparatus as claimed in any one of claims 1 to 7;

wherein the position of the extension member is movable relative to the intramedullary nail holder until the position indicating device indicates that the transducer positioned adjacent the screw receiving aperture is positioned with respect to the at least one transducer located relative to the extension member, such that a drill guided by the drill guide arrangement would enter, or be directed to a location just above, the screw receiving aperture in the intramedullary nail.

In one form the at least two transducers comprises three transducers, wherein the at least one transducer positioned relative to the elongate extension member comprises two transducers located radially equidistant from the elongate extension member, and estimating the position of the transducer positioned adjacent the screw receiving aperture comprises comparing the signal amplitudes of one or more receive signals from each of the two transducers located radially equidistant from the elongate extension member.

According to a third aspect, there is provided a method of generating an offset table for a memory in a controller of an electromagnetic intramedullary nail screw positioning system, the method comprising:

performing a reference calibration using a reference nail with an electromagnetic intramedullary nail screw positioning system prior to surgery;

for each nail in a set of nails types, where each type comprises a unique combination of nail diameter, nail composition and nail length, inserting a nail in the electromagnetic intramedullary nail screw positioning system, measuring an alignment offset of the nail with respect to the reference nail; and storing the set of measured alignment offsets in a memory with the associated nail type.

In one form the method further comprises storing the set of measured alignment offsets in a memory of each of a plurality of electromagnetic intramedullary nail screw positioning system.

In one form the method further comprises fitting a predictive model to the measured alignment offsets, and storing the predictive model in a memory of each of a plurality of electromagnetic intramedullary nail screw positioning system.

According to a third aspect, there is provided a method of use of an electromagnetic intramedullary nail screw positioning system, comprising:

performing a reference calibration using a reference nail with the electromagnetic intramedullary nail screw positioning system prior to surgery;

entering nail identifier into a controller of the electromagnetic intramedullary nail screw positioning system, wherein the controller comprises a memory storing an offset associated with the nail identifier;

using the electromagnetic intramedullary nail screw positioning system to estimate a location of a target aperture in the nail, wherein the offset is applied to one or more positioning measurement from the electromagnetic intramedullary nail screw positioning system to generate an updated estimate of the location of a target aperture in the nail, and the updated estimate is indicated to a user.

In one form, entering a nail identifier comprises entering one or more of a nail diameter, nail composition, nail length and nail side. In a further form, entering a nail identifier comprises entering a product code or catalogue number. In a further form entering a nail identifier comprises scanning a code.

According to a second aspect, there is provided a method for use of an electromagnetic intramedullary nail screw positioning system, comprising:

performing a reference calibration using a reference nail with the electromagnetic intramedullary nail screw positioning system prior to surgery;

entering a nail identifier into a central controller of the electromagnetic intramedullary nail screw positioning system, wherein the central controller comprises a memory storing an alignment offset associated with the nail identifier;

using the electromagnetic intramedullary nail screw positioning system to identify a location of a target aperture in the nail, wherein the alignment offset is applied to positioning measurements.

In one form, entering a nail identifier comprises entering a nail diameter, nail composition, nail length and nail side.

In one form, entering a nail identifier comprises entering a product code or catalogue product code or catalogue number.

In one form, entering a nail identifier comprises scanning a code.

According to a third aspect, there is provided an electromagnetic intramedullary nail screw positioning comprising a central controller comprising a processor and memory, wherein the memory stores a plurality of alignment offsets where each offset is associated with a nail identifier; and the processor is configured to receive a nail identifier from a user, and look up the alignment offset associated with the entered nail identifier, and apply the offset when performing positioning measurements.

BRIEF DESCRIPTION OF DRAWINGS

Embodiments of the present disclosure will be discussed with reference to the accompanying drawings wherein:

FIG. 1A depicts an intramedullary nail and associated screws according;

FIG. 1B depicts an intramedullary nail located and screwed into a femoral bone;

FIG. 2 is a side perspective view of the electromagnetic targeting system according to an embodiment;

FIG. 2A is a schematic diagram of a handle and IntraMedullary Nail of the of the electromagnetic targeting system illustrating the location of the target hole according to an embodiment;

In the following description, like reference characters designate like or corresponding parts throughout the figures.

DESCRIPTION OF EMBODIMENTS

Figure 3:
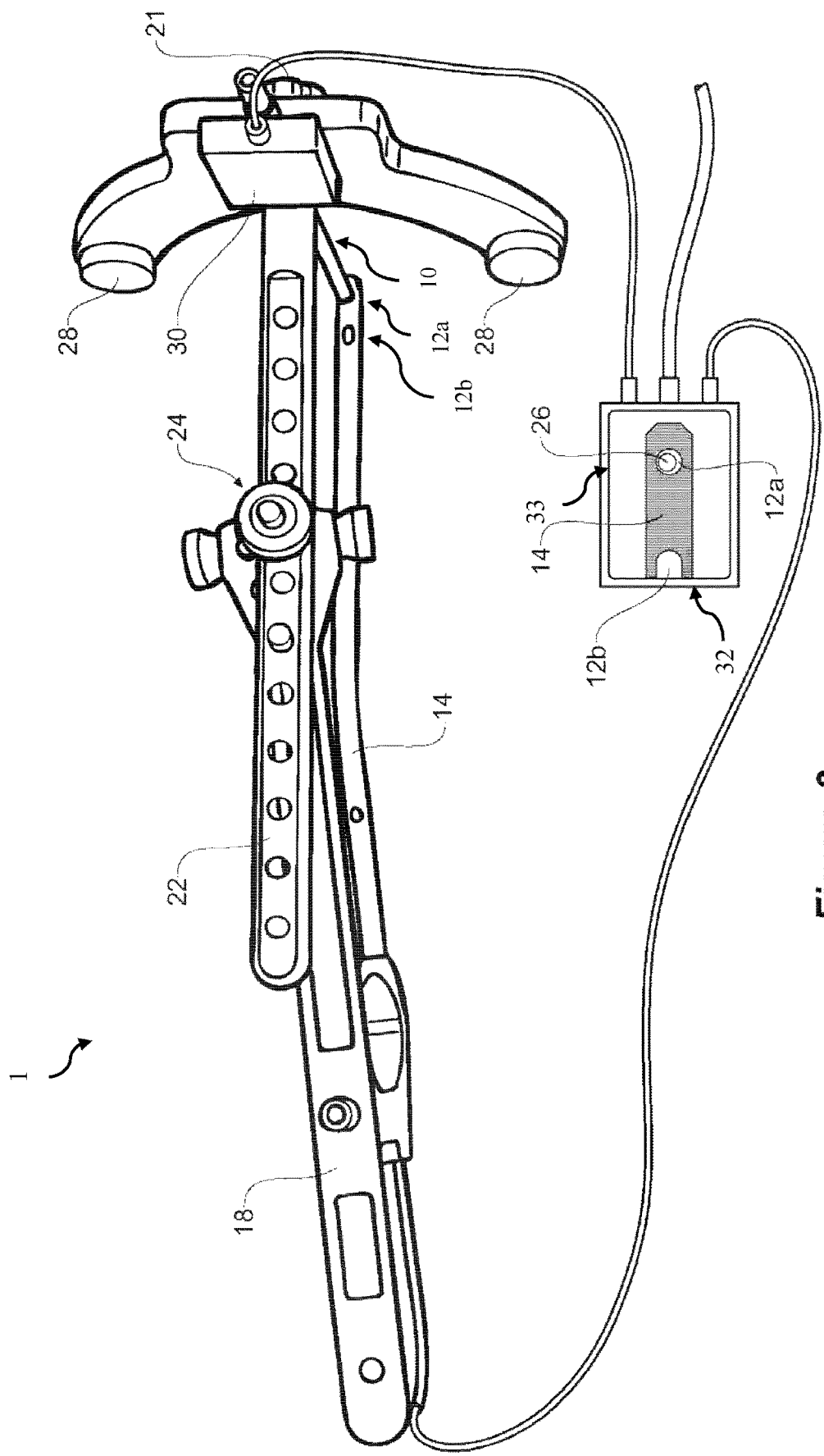
FIG. 3 is a top perspective view of the electromagnetic targeting system of FIG. 2 according to an embodiment.

Embodiments of an electromagnetic intramedullary nail screw positioning system will now be described. This system can be used with a range of IntraMedullary Nail (IMN) of different lengths (or sizes) and materials for treating diaphyseal fractures of long bones, such as (but not limited to) the femur, tibia and humerus, in both adults and children. It will also be understood that the system can be used for other medical treatments where it is deemed advantageous to stabilise the bone through surgical implantation of and IMN, for example in the case of bone disease or a complete break.

FIG. 1A illustrates an example of an IMN 14, which in this case is femoral nail and FIG. 1B illustrates the femoral nail 14 located and screwed into a femoral bone 2, to correct a fracture 3. In this embodiment the IMN 14 includes a plurality of apertures (or holes) 12 for receiving locking screws 4 so that the screws can inserted through bone 2 located about the inserted IMN and through or into the IMN.

In this embodiment the apertures 12 are arranged in a distal pair 12a 12b and a proximal pair 12c 12d. For the sake of clarity proximal and distal are in relation to the point of insertion of the nail into the bone. Thus with the IMN secured to and in place within the bone, the bone is stabilised and able to regenerate supported by the IMN in particular without rotating relative to the bone.

Insertion of the first set proximal screws 4c 4d is relatively easy (in this case only a single proximal screw 4c is inserted). However due to in situ bending of the nail, the locations of the distal apertures 12a 12b into which the distal screws 4a and 4b are to be inserted is relatively unknown, or at least known to insufficient accuracy. In-situ bending of the nail occurs due to a combination of factors. First the geometry of the nails affects the location. IMN are often bent or have a slight curve designed to follow the natural curve of the target bone, so the distal apertures are off-set from an initial axis of the IMN in the proximal end. Further the locations of the distal apertures may be rotated with respect to the nail axis relative to the proximal end. Additionally the composition and length (or size) of the nail 14 will also affect the stiffness (or flexibility/resilience) of the nail. For example IMN are typically formed from stainless steel and/or titanium alloys, and thus the more flexible/resilient (ie less stiff) the material then the greater the variation in location of the distal end. Further the nature of the fracture or break may affect the location of distal end. Whilst jigs can be used to compensate for nail geometry, the effect of material and bone fractures/breaks on the nail are more difficult to predict, and thus a targeting system as described herein may be used to assist in location of the distal apertures 12a 12b to guide the surgeon in drilling holes in the bone to insert fixing screws 4a 4b. As shown in FIG. 1b, the screws will typically pass through the apertures 12 in the nail, and through to the opposing side of the bone (ie completely pass through the bone). However in other embodiments the screws may simply engage with or pass through the nail, and need not pass all the way through the bone. Various shaped apertures and locking screws may be used, including static and dynamic locking systems. Typically an IMN will contain several apertures and the choice of which apertures screws are to be inserted in will typically be a clinical decision based on factors such as size of the bone and type of fracture or break. Further in the context of this specification, distal simply means distal of the proximal end, and the distal apertures need not only be at the distal end of the nail 14, but can be at various points along the nail such as half way along the nail.

Figure 4:
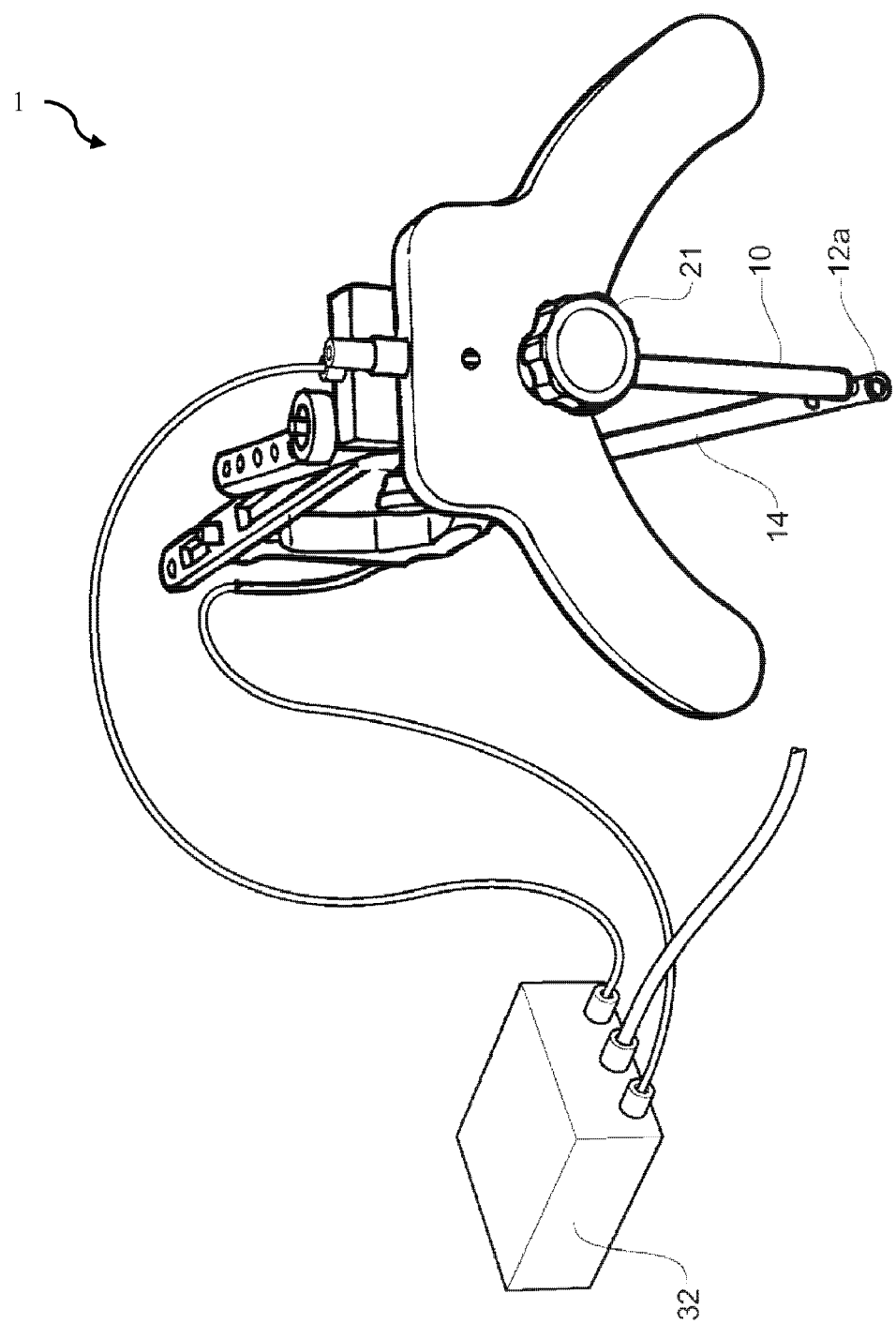
FIG. 4 is an end perspective view of the electromagnetic targeting system of FIG. 2 according to an embodiment.

Referring to FIGS. 2, 3, and 4, an embodiment of an electromagnetic intramedullary nail screw positioning system 1 is illustrated. The system (or apparatus) 1 comprises a drill guide arrangement 10 comprising a drill sleeve guide usable to guide a drill (not shown) towards a distal screw receiving aperture 12a in an intramedullary nail (IMN) 14. It is also possible for the drill guide arrangement to be provided by a wall defining an elongate aperture extending through a housing attached to an elongate extension member, such that it is adapted to guide a drill towards the intended location of the screw receiving aperture in the IMN 14. The drill sleeve guide of the drill guide arrangement 10 in the embodiment depicted in FIGS. 2, 3 and 4 may comprise two parts, the inner sleeve being useable to guide a drill to the required location, and an outer sleeve usable to guide a screw to the prepared opening in the bone formed by the drill. FIG. 4 illustrates those parts at the upper region of the drill sleeve guide.

The system 1 includes a framework having at least three mechanical parts, one of which is the drill guide arrangement 10 previously described, and a further part an intramedullary nail holder 20 (shaped like a handle because it is used by the surgeon to place and manipulate the IMN into place and which also provides a firm support for the remainder of the arrangement) and in its broadest form an elongate extension member 16 extending between the IMN nail holder 20 and the drill guide arrangement 10. In the embodiment illustrated in FIGS. 2, 3 and 4 the elongate extension member 16 is comprised of two parts—a proximal targeting arm 18 and distal targeting arm 22. In use the IMN 14 occupies an existing cannula in the bone 2 being treated. FIG. 2 shows the femur 2 and the outer surface of the leg 3 of the patient having the surgery using dotted lines.

The IMN nail holder 20 is adapted to attach the IMN 14. In this embodiment the attachment arrangement is not shown in the figures but comprises a screw tightened by the surgeon such that one end (proximal end) of the IMN is fixed to the intramedullary nail holder 20. In this embodiment the elongate extension member 16 is comprised of a fixed frame element (or proximal targeting arm) 18 mounted to the intramedullary nail holder 20 and aligned with the longitudinal axis of the IMN 14 at its proximal end and a drill sleeve support element (or distal targeting arm) 22 pivotally mounted to the fixed frame element 18 via pivot arrangement 24. The distal end of the drill sleeve support element 22 (the second elongate element) supports the elongate drill sleeve guide 10.

In one embodiment the pivot arrangement 24 is a threaded screw 24a and knurled disc shaped nut 24b which allows the drill sleeve support element 22 to be clamped or unclamped from the fixed frame element 18 and for those two elements to be rotated relative to each other about the longitudinal axis 27 (FIG. 2) of the pivot arrangement created by the pivot pin 24. There is also (not shown clearly) a slot within the fixed frame element 18 which allows the positioning of the screw laterally of the fixed frame element to better align the longitudinal axis of the drill sleeve support element 22 with the longitudinal axis of the IMN 14 at its distal end. Thus the pivot arrangement permits adjustment of the drill sleeve support element 22 with respect to the fixed frame element 18. The multiple apertures 23 in the drill sleeve support element 22 allow for the extension or retraction of that element with respect to the fixed frame element 18. These are located at predetermined distances which approximately match the length of the IMN 14 and allow positioning of the drill sleeve longitudinal axis 29 (FIG. 2) with the one or more screw receiving apertures in the IMN (12a, 12b, . . . ).

In the embodiment depicted in FIGS. 2, 3 and 4, elongate drill sleeve guide 10 is adjustably mounted with respect to the distal end of the elongate extension member 16 such that an end of the drill sleeve can be spaced away from the IMN 14. Knurled tightening nut 21, partly depicted in FIG. 3 and fully depicted in FIG. 4, is used to loosen and tighten grip on the drill sleeve to permit (vertical) movement of an end of the sleeve closer and further away from the intramedullary nail. The position it is tightened in being a choice made by the surgeon before drilling is commenced.

However in other embodiments other variations are possible. For example the elongate extension member 16 could be single part or comprised of 3 or more parts. FIG. 2A is a schematic illustration of another embodiment in which the elongate extension member 16 is a single part. In this embodiment the IMN nail holder 20 comprises a pivot mount 16a for supporting elongate extension member 16 which supports a drill guide arrangement 10a at the distal end of the elongate extension member 16. This aligns the drill guide arrangement 10a with a distal aperture 12a in the IMN 14. In another embodiment (not shown in any particular detail) there is provided an articulation arrangement between the elongate extension member 16 and the intramedullary nail holder 20, so as to allow movement of the elongate extension member relative to the intramedullary nail holder. The adaption being a mechanical arrangement such as for example, a universal joint with, for example, a friction engagement that can allow infinite variability of the relative position of the elongate extension member to the IMN nail holder and hence the end of the drill sleeve with respect to the distal end of the IMN 14. This friction engagement being not so tight as to still allow a surgeon to adjust the relative position but not so loose as to let the relative position to move unaided. In this embodiment the length of the elongate extension member is such as to match (fixed or adjustable at the adaption end or elsewhere along the elongate extension member) allowing for the positioning of the drill guide arrangement 10a to lie over a screw receiving aperture (e.g. 12a or 12b) in the IMN, this adjustment being done before surgery and then during surgery the length setting remains fixed while the final position of the end of the drill sleeve is guided by the position indicating device (to be described in detail later in the specification)

since the adaption is arranged to allow for movement about an axis of the universal joint such that an end of the drill sleeve can move laterally of the longitudinal axis of the IMN while remaining parallel to the IMN.

The electromagnetic intramedullary nail screw positioning system 1 further comprises at least two positioning transducers. In one embodiment a transducer is a coil (for example an antenna coil) and an associated circuit which can be either configured to transmit a radiofrequency (RF) signal via the associated coil (ie to form a transmitter) or receive a RF signal via the associated coil (ie to form a receiver). That is the positioning transducers may be configured as transmitting transducers or receiving transducers. This may also be referred to as pulse coils and target coils. In the embodiment shown in FIGS. 2, 3 and 4, the system comprises a receive transducer (or target coil) 26 connected to a central controller via receive cable 36 and two transmitting transducers (or pulse coils) 28 connected to the central controller 32 via transmit cable 38. Respective transmit and receive circuits are arranged to communicate to a respective transducer 28/26 for respectively receiving and transmitting signals using a respective transducer. The signal transmission and receiving circuits are used for communicating one or more signals with a respective transducer for respectively receiving and transmitting the one or more signals. Whether there is a transmission or reception by a particular transducer (as long as one is used to transmit and the other/s receive or vice versa) is a design choice, but in this embodiment the transducer 26 is used to receive a signal and the transducers 28 transmit a signal.

The two transmitting transducers are mounted on a symmetrical transducer support member 27 comprising a central portion and two symmetrical arms extending from the central portion. In this embodiment the transducer support member is an inverted wishbone or inverted U shaped piece, and each transducer 28 is mounted near the distal end of each arm. The central portion has central aperture through which the drill sleeve 10 passes, and the interior side of the central comprises an open aperture shaped to receive the elongate extension member 16, such that the transmit support member 27 can rest upon and be supported by the drill sleeve support element 22. A central portion further comprises a bore extending from the exterior side to the interior side for receiving the elongate drill sleeve guide 10 (which passes through both the transducer support 27 and drill sleeve support element 22).

The receive transducer (eg the sensor) 26 is located at the distal end of an insertion tube 34 (or shaft) which is inserted into a central aperture of the nail 14. To ensure correct placement of the receive transducer 26 under the intended aperture 12, markings may be placed along the shaft corresponding the different nail lengths. A stop is locked in place over the marking matching the nail being used 14 such when the shaft is inserted in the central aperture of the nail the stop will engage with the nail holder to prevent further insertion of the shaft and to ensure that the receive transducer 26 is located under the intended aperture 12, or a known distance from the aperture, for the current nail 14.

The transmit transducer are driven by a transmit pulse circuit 30 that generates one or more transmit pulses which is converted by the transmit transducers 28 to a RF transmit signal. The transmit pulse circuit 30 may be mounted to the central portion of the transmit support member, or it may be integrated in the central portion, or the transmit pulse circuit may be located in the central controller 32. The two transmit transducers may be sequentially driven, or they may both be simultaneously driven. The transmit signals may be continuous or pulsed and or a range of wave forms the most basic being sinusoidal and square wave In this embodiment two transmitter transducers 28 are used with a single receiver transducer 26, but other configurations are possible. In one embodiment a single transmit transducer 28 is used which can be positioned on either side of the elongate extension member 22, or more than two transmit transducers may be used. In another embodiment the transmit transducer and the receive transducer locations are reversed, with the transmit transducer located within the nail and a one or two receive transducers located on support arm 27. The software and signals will be reconfigured according to the specific geometrical arrangement used.

When there are two transmitting transducers 28 they are located, as shown in the embodiment illustrated in FIGS. 2 and 3, radially equidistant from the elongate extension member and when in use the longitudinal axis of the intramedullary nail, which would signify that the drill guide is correctly located above the respective screw receiving aperture. The geometry of their location is known to the position indicating device or can be calibrated into the workings of the position indicating device, both techniques being in accord with known techniques.

The central controller 32 comprises a position indicating display device 33 (FIG. 3) that graphically indicates the screw receiving aperture (by using the position of the transducer 26 positioned adjacent the screw aperture) with respect to the axis of the drill guide (by using the two transducers located radially outwardly from the drill sleeve support element 22) such that the drill guide part can be adjusted until the drill guide arrangement (drill sleeve guide 10 in one embodiment) is positioned so that a drill guided by the guide arrangement would enter or be directed to a location just above the screw receiving aperture 12*a* in the IMN 14.

In general the position indicating device 33 is designed primarily for indicating the position of the transducer positioned adjacent the screw receiving aperture relative to the longitudinal axis 29 of the drill guide arrangement using the one or more signals communicated by the signal transmission and receiving circuits (to be described in greater detail later in the specification) which communicate one or more signals between transducers which respectively receive and transmit the one or more signals. However, as described above, the position indicating device is also configured to visually indicate the position in a way that assists the surgeon to position a drill guide arrangement usable to guide a drill towards a screw receiving aperture in an intramedullary nail. It may also be of assistance for the position indicating device to provide a concurrent audible indication of the relative position. In one embodiment the audible signal could have audible sound consisting of a frequency that is low when not aligned and a higher frequency as there is closer alignment and a constant high frequency when acceptable alignment is achieved.

In practical terms, acceptable alignment, whether indicated by the indicating device visually or audibly, indicates where to drill into the bone and then to permit the placement of a screw through and engaging with the bone which will enter the screw receiving aperture in the IMN. The surgeon makes the final determination of the fixing means between the bone and the IMN based on many factors, including in no particular order: the condition of the bone, the angle of entry, the working environment, the time available, etc. wherein the indicating device is a tool to assist the surgeon.

As described, the position of the elongate extension member is movable relative to the nail holder part until the position indicating device indicates that the transducer positioned adjacent the screw receiving aperture is positioned with respect to the at least one transducer located relative to the extension member, such that a drill guided by the drill guide arrangement would enter, or be directed to a location just above, the screw receiving aperture in the intramedullary nail.

In the embodiment described, the movement of the elongate extension member is provided by a pivot arrangement having a pivot axis 27 parallel to the longitudinal axis 29 of the drill guide arrangement (FIG. 2).

Preferably, there are two positioning transducers 28, in this embodiment they are depicted as depending from and positioned along the drill sleeve support element 22 spaced evenly from the drill sleeve support element and on opposite sides of the drill sleeve support element.

The structure that positions and locates these transducers is adapted to be attachable to the drill sleeve support element 22 and there may be an arrangement to allow for fixing that structure in place during use. The ability to attach and un-attach the structure makes the use of the arrangement more manageable during surgery recognising that there is a limb being worked on that surrounds the IMN 14 as well as the need to have parts of the whole device that will be accommodated in an autoclave. Communication between the signal transmission and receiving transducers and associated devices is achieved when required via cable/s 38 and 36 (FIG. 2). A cable can include a conductive inner wire or wires as needed (which may also have individual non-conductive coating) and a non-conductive outer protective coating forming the wire.

The relative position of the transducers is determined by the signals communicated and exchanged by the respective transducers thus indicative of the alignment of the drill sleeve with an aperture in the IMN 14.

The transducer 26 on the free end of cable 36 is guided and carried to a location within the IMN 14 by an insertion tube 34 (FIG. 2) with the cable 36 to the transducer 26 leading back to the position indicating device 33. The insertion tube 34 is also helpfully marked with depth markers which indicate when the distal end of the cable 36 is located below a respective screw receiving aperture 12a, 12b, along the length of the IMN. Since there may be one or more such apertures the insertion tube 34 has a marker to correspond to each so that when aligned with the entrance to the intramedullary nail holder 20, or at some other known position relative to the fixed IMN, provides the surgeon knowledge that the transducer 26 is located below a known respective aperture. In an alternative the cable 36 can be marked as described and the insertion tube 34 is not required.

Materials suitable for autoclaving are used for elements and parts which need repeat use in the sterile operating environment, including for example, the intramedullary nail holder 20, the fixed frame element 18, the drill sleeve support element 22 and associated parts, the transducers 26/28 and associated housings, the insertion tube 34, the cables 36 and 38 extending from respective transducers to the position indicating device 33 (which is not for insertion in to an autoclave). There may however be aseptic connection devices or arrangements to allow for appropriate connection between aseptic and non-aseptic parts within the surgical environment (not shown).

FIG. 3 displays the same elements as described above but depicts an upper view of the arrangement and in particular the position indicating device 33 graphically indicates the positioning of a circle within a representation of the aperture at the end of the IMN 14. The circle representative of the position of the transducer 26 (hence the aperture 12a) is depicted so that when the drill sleeve support element 22 is swung laterally from one side to the other of the IMN about the pivot pin 24 of pivot arrangement (24, 24a and 24b), the circular arc formed is depicted by the side to side movement of a circle relative to the pictorial image of the IMN. The longitudinal location is set predominantly by the apertures in the drill sleeve support element 22 through which, in this embodiment, the pivot pin 24 is inserted and the loosening and fixing of the drill sleeve support element 22 is fixed by the operation of the pivot arrangement elements by a threaded screw 24a and knurled disc shaped nut 24b.

The surgeon thus has a visual indicator (an audible indicator, as described previously, could be used alone or in combination with the visual indicator) so as to allow the surgeon to be assured that when alignment is indicated, a drill can be used to create an aperture in the bone surrounding the IMN 14 and that if drilled far enough through the bone it will appear above the screw receiving aperture 12a in the IMN, such that a screw can be inserted into the created aperture to enter the screw receiving aperture 12a in the IMN.

FIG. 4 is an end on view of the arrangement, depicting the drill sleeve guide 10 usable to guide a drill (not shown) towards a screw receiving aperture 12a in the IMN 14. In this figure the drill sleeve guide 10 is shown with the drill guide position tightening nut 21 for setting the height of the end of the drill sleeve guide above the IMN screw receiving aperture 12a.

The limb and bone of the patient is not shown in FIG. 3 or 4 but it will be appreciated that the surgeon does not have clear visual access to the site of drilling and is guided solely by the apparatus of the invention.

The example of a Femoral Nail depicted in FIG. 1A is an IMN designed for the fixation of proximal and mid-shaft fractures of the femur as depicted in FIG. 1B and FIG. 2. Intended for an ante grade approach, this femoral IMN provides a number of locking modes to provide options for stable fixation. The modes of locking include Static Transverse Locking, Dynamic Transverse Locking and Reconstruction Mode Locking. All the above described nails use locking screws, which are preferably manufactured from non-magnetic material and offer strength and biocompatibility.

In the arrangement described herein, a receiving transducer (target coil) is located in the IMN 14 below a screw receiving aperture, so that an adjustable elongate extension member is positioned correctly when equidistant transmit coils (pulse coils) create equal signals in the receiver coil. When using two transmit transducers (coils), this will occur when the two transmit coils are equidistant from the IMN located receive coil (i.e. located such that the IMN receiving coil receives a detected equal signal strength from each transmit transducer (coil)). One approach is to use signal amplitude but other RF approaches could be used (time of flight, phase based system). The position indicating device 33 is used to provide information to display the alignment in real time based on the signals received.

The electromagnetic targeting system described by embodiments herein preferably includes: high resolution, accuracy and repeatability, having low noise sensitivity, and operates at low power which ensures low emitted electromagnetic radiation and thus minimal interference with medical and other devices in the vicinity. In one embodiment a pulse DC transmission system is used. Pulsed DC operating in a conductive metallic distortion environment must extend the pulse time to allow the transients from the pulse step to dissipate, yielding the rarely accepted fact that speed and distortion rejection are inherently mutually exclusive. Pulsed DC magnetic trackers provide a control of the wait time for the turn-on transient to die out if they are to operate around metals. Allocating additional wait time however, cuts into the cycle time so that more immunity means slower update rates.

In order to distinguish a DC pulse from the earth's magnetic field, one can compete with the DC earth line drawn at about 60,000 nanoTeslas. This is the one factor that forces pulsed DC trackers to typically be larger and definitely heavier and consume more power than AC devices. In many applications, this is of little consequence.

DC tracker information does not disclose latency characteristics and it is expected to be significantly longer, probably in the range of 10-20 milliseconds, because of the need to measure and extract the earth's field from measurements and the sequenced sampling architecture.

Pulsed DC on the other hand, can be designed to be DC coupled and to pass low frequency signals. Temperature stability and offset biases of a DC frontend challenge the circuit designer, as well as being susceptible to much environmental interference. Primary among these is electrical power which is almost always 50 Hz or 60 Hz, so that routing of power or working near strong power fields should ideally be avoided. Other events in this baseband part of the spectrum are voice audio and induced pulses and spikes that have wide bandwidth. Techniques to limit the influence of such interference can make a pulsed DC tracker insensitive to movements in its own sensor, which is the other side of the designer's dilemma.

Consequently, obtaining very stable yet responsive pulsed DC tracking without jitter is a significant challenge. The electromagnetic targeting system was designed to have high resolution, accuracy and repeatability, with low noise, low power and low EMI. In one embodiment the excited transmit coil current follows $$i(t) = Vs/Rs\left(1 - e^{-\frac{t}{T}}\right) \quad (1)$$

where the time constant $T=L/R_t$ and $R_t$ is the sum of supply, coil and switching element resistance.

A constant rate of current change during the pulse (triangular wave-shape) provides a magnetic field containing lower harmonic content than a square edge and importantly a square detector coil voltage. A short pulse length minimises power consumption. Fast fly-back diodes recover some of the energy that is stored in the coil when excitation is removed.

A pair of low resistance air-cored 0.1 mH transmit coils were selected resulting in a total series resistance, including the MOSFET 'ON' resistance, of less than 0.5 ohm per coil. The resulting T of approximately 200 uS provides a steep near triangular current waveform in the inductor during the 40 uS pulse. The pulsed DC variation was chosen so that eddy-currents have time to settle during a "flat-topped" magnetic pulse and can be sampled at this time.

The transducer 26 is in this embodiment is a receive coil having a diameter constrained by the probe inner diameter (ID). A 2 mm 3C90 ferrite rod was selected. This material was designed for use in 125 kHz RFID applications, which closely matches the bandwidth of the 40 uS pulse. The size of the receive pulse follows a turns ratio relationship, i.e. increasing secondary turns increases signal size. 340 turns of 0.125 mm winding wire wound on the ferrite core provided a large clean repeatable receive coil pulse when driven into a 440 ohm balanced load, without saturating the ferrite core material.

The receive pulse edge became significantly rounded (T approximately 7 uS) when surrounded by the stainless steel probe and nail, however, the signal settled sufficiently to allow sampling at t=30 uS. This filtering is considered to be due to eddy-currents driven in the surrounding stainless steel material. The received pulse signal is carried through a twisted pair shielded cable before balanced amplification and filtering by a receiver circuit which provides the pre-processed receive signal to the microcontroller. The microcontroller is configured to perform additional signal processing and estimate the position Significant software filtering was also implemented. A steady repeatable location with 0.1 mm resolution and accuracy has been demonstrated.

Figure 8:
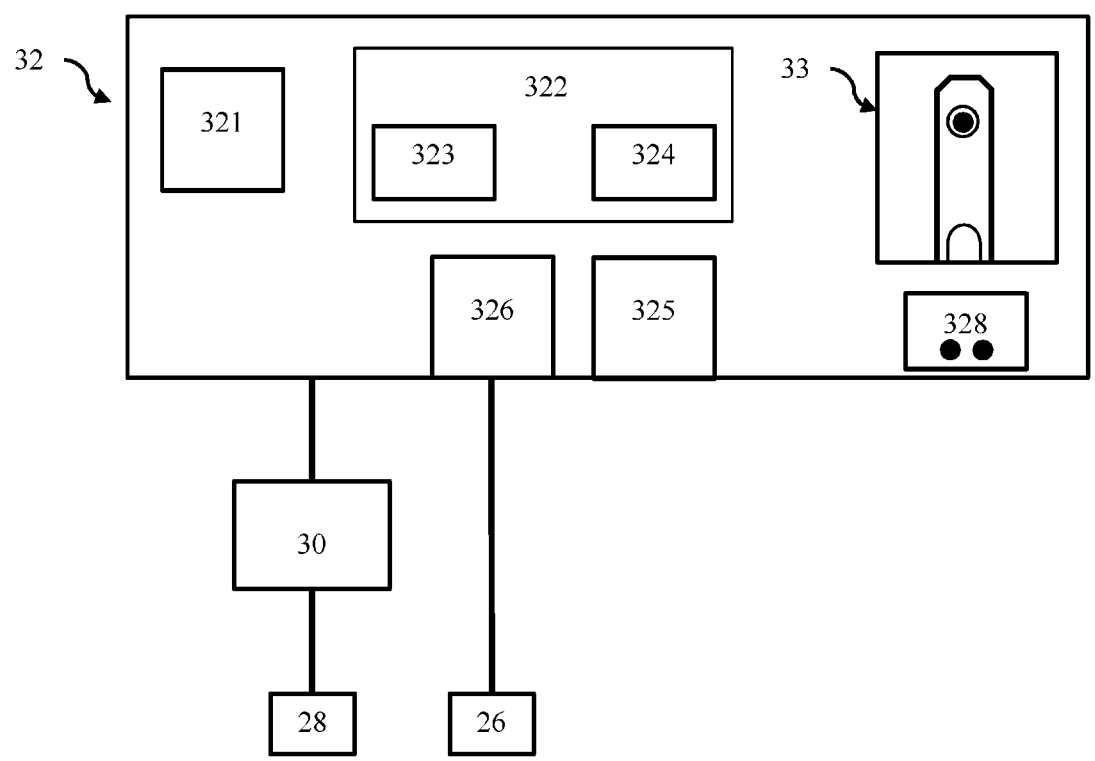

An embodiment of a central controller 32 is illustrated in FIG. 8. The central controller 32 comprises a microcontroller 322 (or microprocessor) comprising a processor 323 and memory 324 which is configured to control the transmit electronics 30 and receive electronics 326. The microcontroller is configured to alternatively switch on the two transmit coils 28 and samples the amplitude of the resultant target coil pulse 26. The microcontroller then calculates the relative position to the centre and displays the calculated position on a display. A display module 33 (or user interface) 33 that may be integrated into the central controller, or external to the central controller (and connected via a wired or wireless connection), displays the location of the drill guide with respect to the nail. In one embodiment the display shows the location over a +5 mm to −5 mm range in 0.1 mm increments (ie 100 increments). Other components such as power supply circuit 321 and a micro SD (µSD) card reader 325, a user input interface 328 (eg switches and diodes) and/or a communications interface may be included. The components may be mounted on a PCB and mounted in a suitable housing. The power circuit may comprise a battery or external power may be supplied via an power socket. In some embodiments the display module 33 is a touch screen which also provides the user input interface 325.

In one embodiment the central controller 32 comprises an integrated display module 33, such as a µLCD-32PT display module from 4D systems (www.4dsystems.com.au). This has two variants, SGC and GFX, the latter intended for applications utilising on-board controller functionality. GFX modules can be programmed to either variation. The module used in the design was purchased as a GFX and was subsequently configured as a SGC that is, as a Serial Graphics Module. Both have touch and audio functionality (not shown in this embodiment).

A number of graphics files are displayed from a removable µSD card inserted in µSD card reader 325 under serial control of microcontroller 322. That is an instruction to display graphics is sent serially from the main PCB. These graphics files are either created on a PC and loaded into a RAW partition on the µSD card or "cached" from slivers of displayed images generated at "startup" if an input switch is held. In this mode, 101 target circles are drawn over the background graphic and saved. These slivers can be called and displayed rapidly. In one embodiment the "cached slivers" (described above) must be created by holding down the input switch during startup whenever a new microSD (µSD) card is fitted or a new background image is saved to the card.

The μSD card is initialised by removing the card and inserting it in a μSD to SD carrier in a PC and running a removable media partition tool (eg a RMPET utility) on that PC. To initialise a new card, choose the SD drive, delete its partition table, remove and replace SD card carrier, Choose Partition Parameters, Create/Alter partition table 50% FAT and 50% non FS (RAW). A Graphics Composer is used to save images to the μSD card (in the carrier and connected to a PC). The steps comprise: Add entry, find bitmap file (eg imndg2.bmp), set screen size (320×240 landscape), then build and save gcs file (project) to card, Build choosing uSD Raw at specified offset. Offset for Logo (Splash screen) is 0. Background image (nail, logo, title) is at 512. The μLSD card can then be inserted back into the μLCD-32PT. For reference, the cache images (slivers) are each 128 bytes and begin at 2048.

In another embodiment the central controller 32 including the graphics display 33 is implemented in a portable computing device such as a tablet computing device, or a smart phone running an app which implements the above functionality. In this embodiments cables 36 and 38 between the transducers 26, 28 and the central controller 32 are omitted, and the portable computing device wirelessly communicates with circuits 30 325 associated with transducers 26, 28 using a wireless protocol, such as a radio frequency protocol including Bluetooth, ZigBee, WiFi Direct, or optical protocols including IRDA, or other protocols. In this embodiment the local transmitter circuit 30 is associated with the transmit transducers 28 and includes a communications circuit, a power supply and a transmit circuit for generating a transmit pulse. The communications circuit receives a control signal from the central controller 32 to instruct the transmit circuit to transmit a pulse. The control signal may be simply be a trigger signal and the local transmitter circuit determines or controls the transmit parameters, or the control signal may contain transmit parameters used by the transmit circuit to transmit the control signal. A local receiver circuit 325 is associated with the receive transducer 26 and comprises a power supply, a communications circuit and a receive circuit processing a receive pulse (or signal). The communications circuit receives a control signal to wake up or instruct the receive circuit to listen for a receive signal, and to transmit the processed receive signal back to the central controller to allow an estimate of the location of the nail to be displayed.

The system can be used with a wide variety of nails of different lengths (sizes), diameters and compositions for a range of bones and patient sizes including paediatric patients. For example the Austofix Sophos range includes PHN standard and long nails that may be used for the humerus, the F1, F2, F3 and S2 ranges from the femur, and Austofix UTN for the tibia. Typical compositions include stainless steel and titanium alloys, typical diameters are 7, 8, 9, 10, 11, 12, and 13 mm, and typical lengths are between 170 mm and 420 mm. This range of nails comprises approximately 200 different nail configurations.

In addition to nail type (eg femoral, tibial etc) the specific nail length, nail diameter and composition of the nail affects the transmission properties of the pulse through the nail, as the combination will give rise to different eddy currents in the material and these effects prevent the use of a single calibration for all nail types. For example the A-P bend of femoral nails causes variation with different nail lengths. Additionally it has been discovered that the rotary alignment of the nail to the transmitter around the axis of the drill sleeve can also affect the sensitivity. Accordingly a specific calibration is required for each nail.

Thus in one embodiment the system is calibrated during surgery using the specific nail selected for the surgery. This involves the surgeon (or other surgical staff) inserting the sterile nail 14 into the intramedullary nail holder 20, inserting the sensor transducer 26 into the shaft of the nail, placing the support arm 27 one the drill sleeve support element 22, and then adjusting the orientation (eg via pivot arrangement 24) until the drilling sleeve 10 in the support arm 27 is aligned with the target aperture in the nail. At this point the user presses a set button on the controller 32 to inform the controller the system is aligned. This is performed away from metallic components and electromagnetic sources which may distort the electromagnetic field around the nail and thus lead to an erroneous calibration. The system is then disassembled, and the nail 14 is inserted into the bone of the patient followed by insertion of the sensor transducer 26 into the shaft of the nail. The framework is then reassembled on the patient with the support arm, and the calibrated system is used to align the drilling sleeve with the target aperture using the display module. Once the drilling sleeve is aligned, the surgeon drills the holes and inserts the screws.

It has been discovered that for a given nail type, or configuration, the nail to nail variation for nails of the same type, is much less than the variation from nail type to nail type. This enables an improved calibration system to be utilised which avoids the need for the surgeon to calibrate the system during surgery. This reduces the risk of an incorrect calibration procedure, reduces the risk of contamination of the nail 14, and significantly reduces the surgical time (thus increasing surgical throughput and reducing the cost of surgery). In this embodiment the system (eg via memory 324) is configured to store an alignment offset for each nail type (or nail configuration) in a set of possible nail types (or configurations) with respect to a reference nail in a memory of the central controller, for example in an alignment offset table, which may be a database, a file or other data structure. In this embodiment a reference calibration is performed on a reference nail as described above which zeros the system. Once this reference calibration is performed on a specific positioning system, then the surgeon needs only to input the type of nail being used to the central controller 32 for that system, and the controller will look up the associated alignment offset for the input nail type, and apply that alignment offset to all future measurements (until the next nail type is entered). The positioning system can be periodically recalibrated as desired, for example every 3, 6, or 12 months using the reference nail. Additionally the alignment offset table stored by the memory can be updated as new nail configurations are manufactured, or updated alignment offsets are made available.

In one embodiment the alignment offsets are obtained by using a reference positioning system, a reference nail, and a set of nails where each nail in the set is a different type, that is has a different combination of features such as nail type, length, diameter, composition, etc. The system is calibrated as above for the reference nail type. Then the nail is replaced with a nail from the set of nail types, physically aligned in the system and the alignment offset is measured (ie the deviation from 0) and recorded. This may be recorded at 0.1 mm resolution (ie to align with display elements which are shown at 0.1 mm resolution) or the exact offset may be measured and stored (eg 0.0751 mm). This procedure is repeated for each nail in the set of nail types, and the alignment offsets are stored in a database. To improve robustness this method may be repeated with multiple positioning systems on the same reference nail and set of nails, and/or repeated measurements for each nail, or measurements are made for multiple nails of the same type, where multiple measurements are made these may be averaged.

Figure 7:
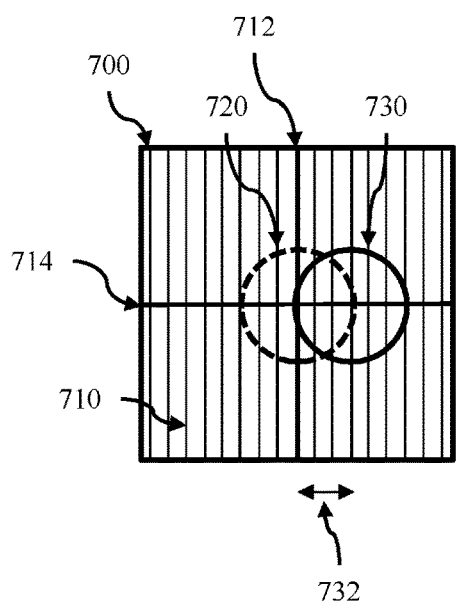
FIG. 7 is a schematic diagram of an alignment offset measurement according to an embodiment and FIG. 8 is a schematic diagram of a central controller apparatus according to an embodiment.

FIG. 7 shows a schematic diagram of an alignment offset measurement according to an embodiment. The screen 700 comprises alignment markers 710 such as vertical lines across the field of view. The screen and a cross hair defined by vertical line 712 and horizontal line 714 are centred on the reference alignment location 720, indicated by a dashed circle. This represents the aligned position with the reference nail. A measurement is taken with a different nail and the alignment offset 732 measured using the alignment markers 710 with respect to the reference position (vertical cross hair line 712). The alignment markers may be an indication of physical distance (eg each is spaced at 0.1 mm) or it may be a marker identifier (eg marker 3) or a number of pixels on the display which can then be used by directly the by display software. That is actual physical distance does not need to be known, just a consistent distance on the display.

The alignment offset for each nail type is then stored along with associated identifying data. This associated identifying data may be the nail specifications, such as nail type, composition, diameter and length, and the user interface may require the surgeon or user to enter this information to the controller 32 at the start of the surgery (for example a left 10 mm cannulated F2 Femoral nail with a length 360 mm). Alternatively a nail identifier (which may be a product code or catalogue number, or some other reference) may be associated with a nail type, and this nail identifier stored with the nail type (and alignment offset). In this case the surgeon or user need only enter the nail identifier (nail product code: 356036) and the system can look up the alignment offset using this reference. In another embodiment a bar code, QR code, or other scannable code may be associated with the nail type. In this case the surgeon or user need only scan the code (using a reader incorporated in the controller 32), and the system will look up the alignment offset associated with the code. In another embodiment an image of the product packaging (or a part of the packaging) may be associated with the nail type. In this case the surgeon or user need only take a photo of the product packaging, and the system will perform image recognition to identify the matching product packaging, and thus the nail type, and the associated alignment offset.

In another embodiment, a predictive model of the alignment offsets is stored by the central controller 32. In this embodiment, the surgeon (or user) enters the nail parameters such as composition, diameter and length and nail side (left or right). In the case of femoral nails the anterior-postal (AP) bend can affect the rotary alignment of the nail to the transmitter around the axis of the drill sleeve, and this can lead to variations in offsets with nail lengths. This effect is normally taken into account through entering the nail type and length, but in other embodiments the system could be further configured to detect the rotary alignment, for example with an orientation sensor (eg gyroscope and/or accelerometers). Alternatively a marked reference device could be used to allow a user to measure and then enter the rotary alignment so that it can be used to obtain the correct offset.

These nail parameters are then provided to the predictive model which estimates the alignment offset, and this alignment offset is then used by the system. The predictive model can be obtained by performing a statistical analysis on a set of measurements obtained using one or more positioning systems with one or more sets of nails (with one or more nails for each nail type in the set). That is, the method comprised fitting a statistical model to the data in the alignment offset table above, and the model parameters are stored in the memory 324 so that they can then be used to predict the alignment offset for any input nail, using interpolation or extrapolation. Variance estimates of model parameters can be used to set limits on allowable interpolation or extrapolation (ie the range over which interpolated or extrapolated values are expected to be of sufficient accuracy).

In some embodiments there are 5 independent variables—nail type (femoral, tibial etc), nail diameter, nail length, material (stainless or titanium), and nail side. In the case of nail side (left or right), typically the side only affects the sign (+/−) of the offset rather than the magnitude of the offset and so this variable can effectively be eliminated. That is a single offset is stored for a nail type, and entering the side determines the sign of the offset. Also as mentioned above, the anterior-postal (AP) bend in some femoral nails can affect the rotary alignment of the nail to the transmitter around the axis of the drill sleeve, and this can lead to variations in offsets with nail lengths. However this effect (if present) is normally taken into account through entering the nail type and length, but in other embodiments, including for other nails where similar rotary variations can occur, then this could be another variable, and the system could be further configured to detect the rotary alignment, for example with an orientation sensor (eg gyroscope and/or accelerometers) or it could be measured and entered using a marked reference device. An additional variable can also arise when there are multiple holes in the distal end of the nail which can each be separately targeted. In this case a separate offsets may be determined and stored for each hole.

Whilst there are several independent variables, these have different magnitudes, and thus the model need not include the independent variables with small effects. For example it has been discovered that the largest source of variance is the diameter, followed by the locations of the proximal and distal apertures, with length and material composition having the least influence on differences in alignment offsets (with stainless steel and titanium appearing mostly identical). Thus a model can be generated in which the diameter is the most influential parameter in determining alignment offsets, or model including diameter, location and type or length effects. As mentioned above the rotary alignment of the nail to the transmitter around the axis of the drill sleeve can also affect the offset. This mostly occurs in relation to femoral nails where the location of the AP bend leads to variations with length. Thus including type or length in the model can effectively take this into account, and these variables can be entered by a user to allow determination of the correct alignment offset to be used. Alternatively the alignment offset can be explicitly taken into account in the model. In this case measurements may be obtained as part of the calibration process and the system can either measure offsets or users can enter measurements.

Figure 5:
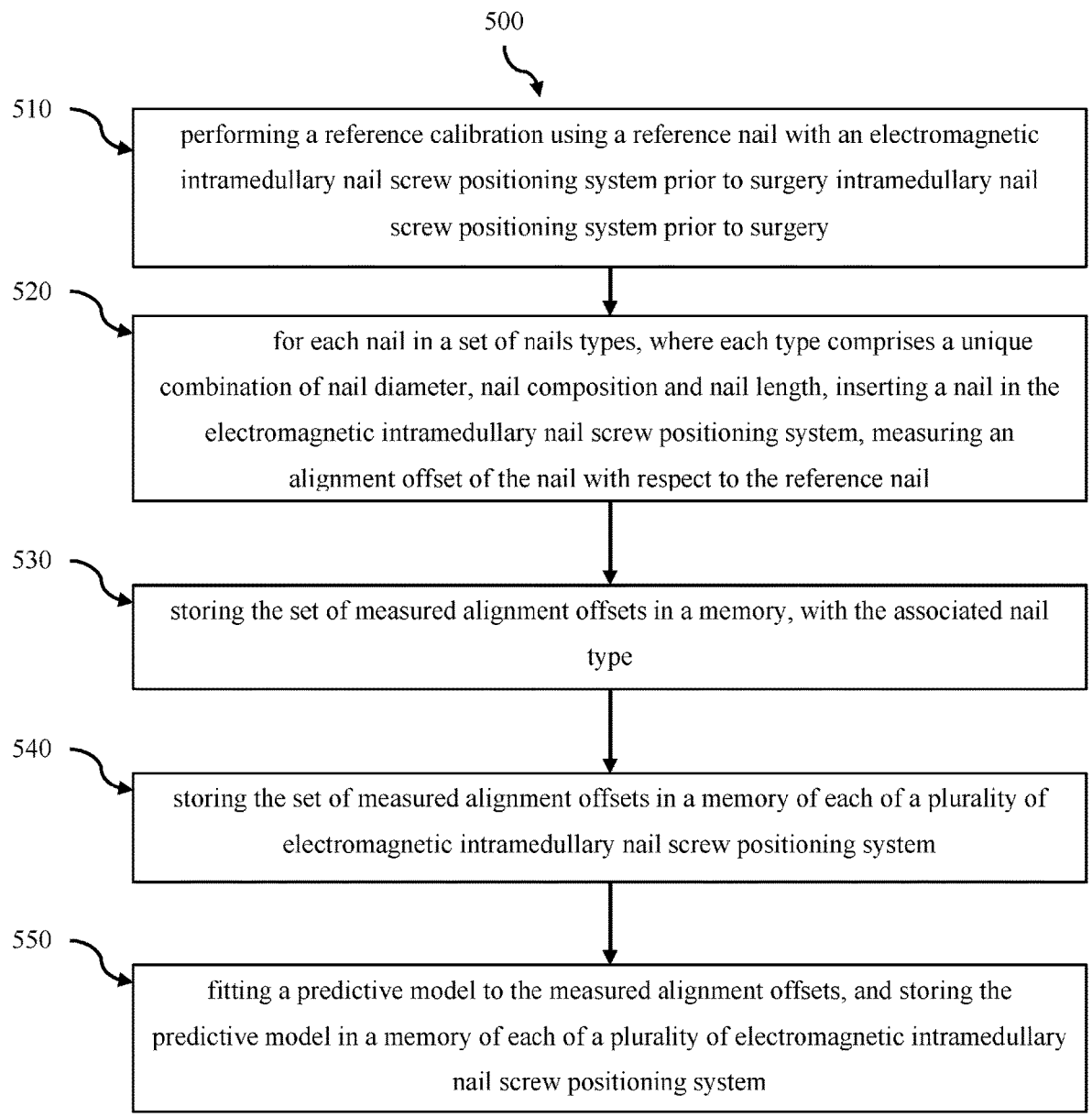
FIG. 5 is a flow chart of a method of generating an offset table for an electromagnetic intramedullary nail screw positioning system according to an embodiment.
Figure 6:
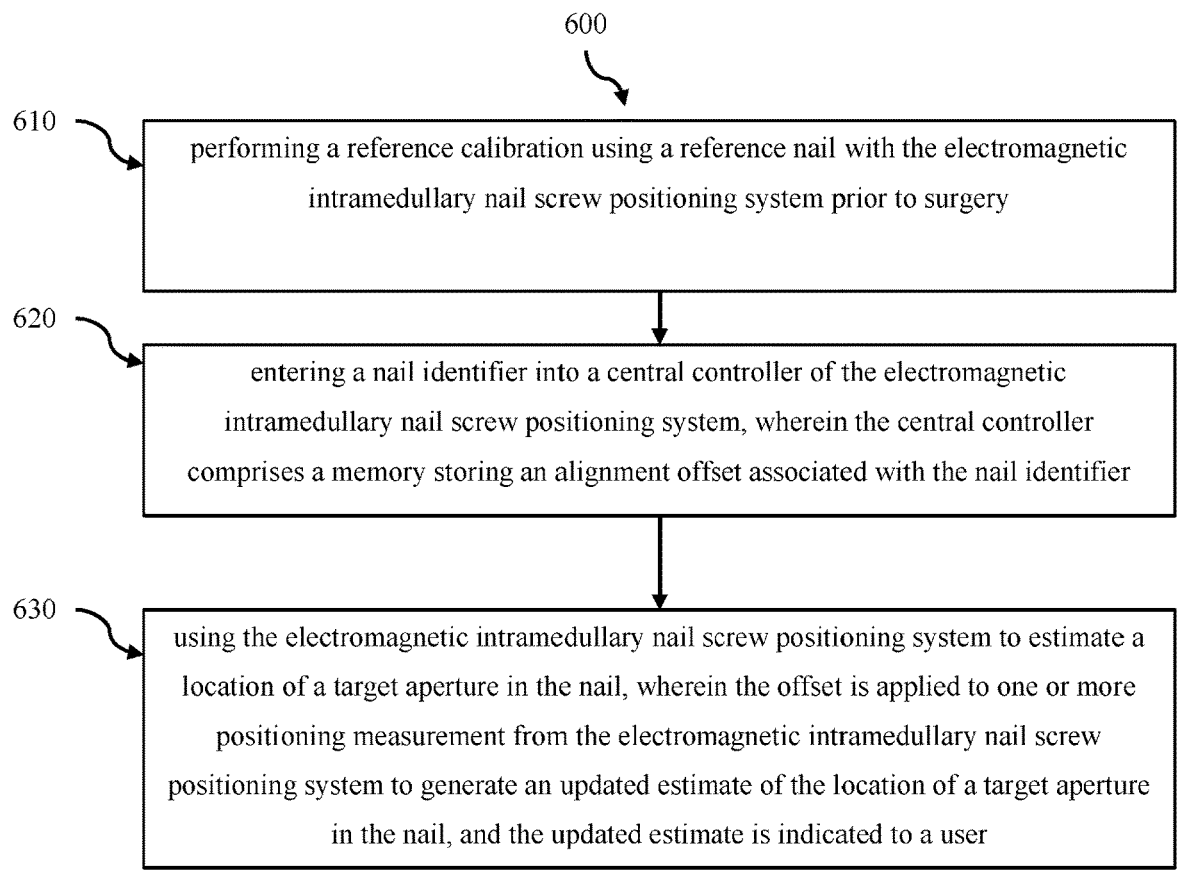
FIG. 6 is a flow chart of a method for use of an electromagnetic intramedullary nail screw positioning system according to an embodiment.

These methods are further illustrated in FIGS. 5 and 6. FIG. 5 is a flow chart of a method 500 of generating an offset table for an electromagnetic intramedullary nail screw positioning system according to an embodiment. Step 510 comprises performing a reference calibration using a reference nail with an electromagnetic intramedullary nail screw positioning system prior to surgery. Step 520 comprises, for each nail in a set of nails types, where each type comprises a unique combination of nail diameter, nail composition, nail side, and nail length, inserting a nail in the electromagnetic intramedullary nail screw positioning system, measuring an alignment offset of the nail with respect to the reference nail.

Step 530 comprises storing the set of measured alignment offsets in a memory, with the associated nail type. Optional step 540 comprises storing the set of measured alignment offsets in a memory of each of a plurality of electromagnetic intramedullary nail screw positioning system. Optional step 550 comprises fitting a predictive model to the measured alignment offsets, and storing the predictive model in a memory of each of a plurality of electromagnetic intramedullary nail screw positioning system.

This method may be varied or modified based on the range of nails used. For example the rotary alignment of the nail to the transmitter around the axis of the drill sleeve can affect the offset. In particular, the anterior-postal bend of femoral nails causes variation with different nail lengths. If measurements are made and stored for a range of nail lengths, then this can be looked up based on the entered nail type and length. Alternatively during calibration this effect may be explicitly measured at a range of rotary alignments (including a predefined set of alignments) so that the effect can be predicted or otherwise taken in account based on the entered data by the user. In another variation, nails may have multiple holes in the distal end of the nail which can each be separately targeted. In this case a separate offsets may be determined and stored for each hole. Then, during use, the surgeon (or user) would be required to further enter a nail hole index or label for the hole they are targeting such as numerical index of from the distal end (1, 2, 3, etc) or a label such as proximal hole or distal hole (in the case of two holes both at the distal end) to ensure the correct offset is determined. This could be performed as part of the step of entering a nail identifier. In another embodiment the left and right offsets may be of identical magnitude but opposite sign (ie mirror image offsets about a zero point). In this case a single set of offsets may be obtained and stored for a nail, and in use, entering the left or right side is used determine the sign of the offset. In one embodiment software could ask for a minimum set of nail parameters (for example based on those which have the greatest influence) such as nail diameter, length and type, and provide an option to enter further parameters such as side (left or right) or hole index/label (eg 1, 2, or 3; or proximal or distal) for nails where there are multiple distal holes.

FIG. 6 is a flow chart of a method 600 for use of an electromagnetic intramedullary nail screw positioning system according to an embodiment. Step 610 comprises performing a reference calibration using a reference nail with the electromagnetic intramedullary nail screw positioning system prior to surgery. Step 620 comprises entering a nail identifier into a central controller of the electromagnetic intramedullary nail screw positioning system, wherein the central controller comprises a memory storing an alignment offset associated with the nail identifier. Step 630 comprises using the electromagnetic intramedullary nail screw positioning system to estimate a location of a target aperture in the nail, wherein the offset is applied to one or more positioning measurement from the electromagnetic intramedullary nail screw positioning system to generate an updated estimate of the location of a target aperture in the nail, and the updated estimate is indicated to a user.

The system described herein provides an improved positioning system compared to previous systems. Further the calibration method using stored calibration offsets reduces the risk of an incorrect calibration procedure, reduces the risk of contamination of the nail, and significantly reduces the surgical time, thus increasing surgical throughput and reducing the cost of surgery.

Those of skill in the art would understand that information and signals may be represented using any of a variety of technologies and techniques. For example, data, instructions, commands, information, signals, bits, symbols, and chips may be referenced throughout the above description may be represented by voltages, currents, electromagnetic waves, magnetic fields or particles, optical fields or particles, or any combination thereof.

The processing of signals may be performed directly in hardware, in a software module executed by a processor, or in a combination of the two. For a hardware implementation, processing may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof. Software modules, also known as computer programs, computer codes, or instructions, may contain a number of source code or object code segments or instructions, and may reside in any computer readable medium such as a RAM memory, flash memory, ROM memory, EPROM memory, registers, or any suitable form of computer readable medium.

In one embodiment the processing is performed by a computer apparatus comprising one or more central processing units (CPU), a memory, and an Input/Output (or Communications) interface, and may include a graphical processing unit (GPU), and input and output devices. The CPU may comprise an Input/Output Interface, an Arithmetic and Logic Unit (ALU) and a Control Unit and Program Counter element. The Input/Output Interface may comprise lines or inputs for receiving signals or data from the load cell module, switch module, indicator module and communications module. The communications interface is configured to communicate with a communications module in another device using a predefined communications protocol which may be wireless or wired (eg Bluetooth, Zigbee, IEEE 802.15, IEEE 802.11, TCP/IP, UDP, etc). The computing apparatus may comprise a single CPU (core) or multiple CPU's (multiple core), or multiple processors. The computing apparatus may be a server, desktop or portable computer and may use a parallel processor, a vector processor, or may be part of a distributed (cloud) computing apparatus. The memory is operatively coupled to the processor(s) and may comprise RAM and ROM components, and secondary storage components such as solid state disks and hard disks, flash memory (SD cards), which may be provided within or external to the device. The memory may comprise instructions to cause the processor to execute a method described herein. The memory may be used to store the operating system and additional software modules or instructions. The processor(s) may be configured to load and execute the software code, modules or instructions stored in the memory. The computing apparatus may comprise additional electronic modules or boards to perform signal conditioning or pre-processing, and signal processing. The computing apparatus may include a chargeable battery As used herein, a phrase referring to "at least one of" a list of items refers to any combination of those items, including single members. As an example, "at least one of: a, b, or c" is intended to cover: a, b, c, a-b, a-c, b-c, and a-b-c.

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers.

The reference to any prior art in this specification is not, and should not be taken as, an acknowledgement of any form of suggestion that such prior art forms part of the common general knowledge.

It will be appreciated by those skilled in the art that the disclosure is not restricted in its use to the particular application or applications described. Neither is the present disclosure restricted in its preferred embodiment with regard to the particular elements and/or features described or depicted herein. It will be appreciated that the disclosure is not limited to the embodiment or embodiments disclosed, but is capable of numerous rearrangements, modifications and substitutions without departing from the scope as set forth and defined by the following claims.

The invention claimed is:

1. A control apparatus for an electromagnetic intramedullary nail screw positioning system for positioning a drill guide arrangement usable to guide a drill towards a screw receiving aperture in an intramedullary nail, the apparatus comprising:
   at least one processor, at least one memory, and a user interface,
   wherein the at least one memory comprises a plurality of alignment offset values, each alignment offset value associated with an intramedullary nail identifier that is also associated with a nail type, and the at least one memory comprises instructions to cause the at least one processor to:
   receive an intramedullary nail identifier from a user via the user interface;
   send at least one control signal to one or more signal transmission and receiving circuits to transmit one or more signals from at least one transducer;
   receive at least one receive signal from one or more signal transmission and receiving circuits from at least one transducer;
   estimate the position of the transducer positioned adjacent the screw receiving aperture relative to the longitudinal axis of the drill guide arrangement using the at least one receive signal;
   determine an alignment offset value using the received intramedullary nail identifier;
   apply the determined alignment offset to the estimate the position of the transducer to obtain an updated estimate; and
   indicate the updated estimate of the position of the transducer positioned adjacent the screw receiving aperture relative to the longitudinal axis of the drill guide arrangement using the user interface.

2. The control apparatus as claimed in claim 1, wherein the received nail identifier comprises at least a nail diameter, a nail composition, a nail length and a nail side.

3. The control apparatus as claimed in claim 1, wherein the received nail identifier comprises a product code or catalogue number.

4. The control apparatus as claimed in claim 1, wherein the control apparatus comprises a barcode scanner, and the nail identifier is received from the barcode scanner.

5. The control apparatus as claimed in claim 1, wherein the plurality of alignment offset values are stored as an offset table in the at least one memory, wherein each offset is associated with a nail identifier.

6. The control apparatus as claimed in claim 5, where the plurality of alignment offset values are obtained from a reference calibration process performed prior to a surgical procedure, wherein the reference calibration process comprises:
   performing a reference calibration using a reference nail with an electromagnetic intramedullary nail screw positioning system;
   for each nail in a set of nails types, where each type comprises a unique combination of nail diameter, nail composition and nail length, measuring an alignment offset of an inserted nail in the electromagnetic intramedullary nail screw positioning system with respect to the reference nail; and
   storing the set of measured alignment offsets in the at least one memory with each associated nail type.

7. The control apparatus as claimed in claim 1, wherein the control apparatus comprises a display, and indicating the updated estimate of the position of the transducer comprises visually indicating the updated estimate of the position of the transducer positioned adjacent the screw receiving aperture relative to the longitudinal axis of the drill guide arrangement.

8. An electromagnetic intramedullary nail screw positioning system comprising:
   a) a framework including:
      an intramedullary nail holder adapted to attach to an intramedullary nail;
      an elongate extension member extending from the intramedullary nail holder adapted to allow movement of the elongate extension member relative to the intramedullary nail holder; and
      an elongate drill guide arrangement associated with the elongate extension member so that the longitudinal axis of the drill guide arrangement is orientated substantially towards the intramedullary nail;
   b) at least two transducers, one transducer positioned in the intramedullary nail adjacent one of the screw apertures, and at least one transducer positioned relative to the elongate extension member;
   c) one or more signal transmission and receiving circuits for communicating one or more signals with a respective transducer for respectively transmitting and receiving the one or more signals;
   d) a control apparatus comprising:
   at least one processor, at least one memory, and a user interface,
   wherein the at least one memory comprises a plurality of alignment offset values, each alignment offset value associated with an intramedullary nail identifier that is also associated with a nail type, and the at least one memory comprises instructions to cause the at least one processor to:
   receive an intramedullary nail identifier from a user via the user interface;
   send at least one control signal to the one or more signal transmission and receiving circuits to transmit one or more signals from at least one of the at least two transducers;
   receive at least one receive signal from the one or more signal transmission and receiving circuits from at least one of the at least two transducers;
   estimate the position of the transducer positioned adjacent the screw receiving aperture relative to the longitudinal axis of the drill guide arrangement using the at least one receive signal;
   determine an alignment offset value using the received intramedullary nail identifier;

apply the determined alignment offset to the estimate of the position of the transducer to obtain an updated estimate; and indicate the updated estimate of the position of the transducer positioned adjacent the screw receiving aperture relative to the longitudinal axis of the drill guide arrangement using the user interface; and wherein the position of the elongate extension member is movable relative to the intramedullary nail holder until the position indicating device indicates that the transducer positioned adjacent the screw receiving aperture is positioned with respect to the at least one transducer located relative to the elongate extension member, such that a drill guided by the drill guide arrangement would enter, or be directed to a location just above, the screw receiving aperture in the intramedullary nail.

9. The system as claimed in claim 8, wherein the at least two transducers comprises three transducers, wherein the at least one transducer positioned relative to the elongate extension member comprises two transducers located radially equidistant from the elongate extension member, and estimating the position of the transducer positioned adjacent the screw receiving aperture comprises comparing the signal amplitudes of one or more receive signals from each of the two transducers located radially equidistant from the elongate extension member.

10. A method for use of an electromagnetic intramedullary nail screw positioning system, comprising:

performing a reference calibration using a reference nail with the electromagnetic intramedullary nail screw positioning system prior to surgery;

entering a nail identifier into a controller of the electromagnetic intramedullary nail screw positioning system, wherein the controller comprises a memory storing an offset associated with the nail identifier;

using the electromagnetic intramedullary nail screw positioning system to estimate a location of a target aperture in the nail, wherein the offset is applied to one or more positioning measurement from the electromagnetic intramedullary nail screw positioning system to generate an updated estimate of the location of a target aperture in the nail, and the updated estimate is indicated to a user.

11. The method as claimed in claim 10, wherein entering a nail identifier comprises entering at least a nail diameter, a nail composition, a nail length and a nail side.

12. The method as claimed in claim 10, wherein entering a nail identifier comprises entering a product code or catalogue number.

13. The method as claimed in claim 10, wherein entering a nail identifier comprises scanning a code.

14. The system as claimed in claim 8, wherein the received nail identifier comprises at least a nail type, a nail diameter, a nail composition, a nail length and a nail side.

15. The system as claimed in claim 8, wherein the received nail identifier comprises a product code or catalogue number.

16. The system as claimed in claim 8, wherein the control apparatus comprises a barcode scanner, and the nail identifier is received from the barcode scanner.

17. The system as claimed in claim 8, wherein the plurality of alignment offset values are stored as an offset table in the at least one memory, wherein each offset is associated with a nail identifier.

18. The system as claimed in claim 17, wherein the plurality of alignment offset values are obtained from a reference calibration process performed prior to a surgical procedure, wherein the reference calibration process comprises:

performing a reference calibration using a reference nail with an electromagnetic intramedullary nail screw positioning system;

for each nail in a set of nails types, where each type comprises a unique combination of nail diameter, nail composition and nail length, measuring an alignment offset of an inserted nail in the electromagnetic intramedullary nail screw positioning system with respect to the reference nail; and storing the set of measured alignment offsets in the at least one memory with each associated nail type.

19. The system as claimed in claim 8, wherein the control apparatus comprises a display, and indicating the updated estimate of the position of the transducer comprises visually indicating the updated estimate of the position of the transducer positioned adjacent the screw receiving aperture relative to the longitudinal axis of the drill guide arrangement.

* * * * *